United States Patent [19]

Bunce

[11] Patent Number: 5,401,254
[45] Date of Patent: Mar. 28, 1995

[54] CARTRIDGES FOR DISPENSING GEL-LIKE SUBSTANCES

[75] Inventor: Philip Bunce, Portland, Australia

[73] Assignees: Enzacor Australia Pty. Ltd.; Portland Surgical Prod. Pty. Ltd., both of Australia

[21] Appl. No.: 852,778

[22] Filed: Mar. 17, 1992

[51] Int. Cl.⁶ .............................................. A61M 5/315
[52] U.S. Cl. ..................................... 604/218; 222/386; 604/57
[58] Field of Search ................ 604/57, 73, 187, 218, 604/225, 232; 222/326, 327, 386

[56] References Cited

U.S. PATENT DOCUMENTS

| 659,130 | 10/1900 | Bucklin | 604/187 |
|---|---|---|---|
| 1,393,138 | 10/1921 | Kelley | 222/386 |
| 2,178,840 | 11/1939 | Lorenian | 604/57 |
| 2,695,735 | 11/1954 | Van Doornik | 222/386 |
| 2,754,822 | 7/1956 | Emelock | 604/218 |
| 2,755,003 | 7/1956 | Sherbondy | 222/327 |
| 2,847,011 | 8/1958 | Jones | 604/232 |
| 2,955,627 | 10/1960 | Gaskins | 222/386 |
| 3,884,396 | 5/1975 | Gordon et al. | 222/327 |
| 3,923,208 | 12/1975 | Bergloff | 222/386 |
| 4,637,531 | 1/1987 | Olsson | 222/387 |
| 4,846,801 | 7/1989 | Okuda et al. | 604/218 |

FOREIGN PATENT DOCUMENTS

| 144483 | 6/1985 | European Pat. Off. | 604/187 |
|---|---|---|---|
| 2142245 | 1/1985 | United Kingdom | 604/187 |

Primary Examiner—Ralph A. Lewis
Attorney, Agent, or Firm—Harness, Dickey & Pierce

[57] ABSTRACT

A cartridge for dispensing a substance in a gel-like form comprises a body having a discharge nozzle at its forward end and a piston movable through the body to dispense the product through the nozzle. The interior configuration of the nozzle is such as to prevent dripping of the substance from the nozzle if the cartridge is inverted and preferably this effect is obtained by forming the interior of the nozzle with a venturi-like profile.

4 Claims, 1 Drawing Sheet

CARTRIDGES FOR DISPENSING GEL-LIKE SUBSTANCES

BACKGROUND OF THE INVENTION

1. Field of the Invention

The present invention relates to a cartridge for dispensing a gel-like substance and more particularly to a cartridge for dispensing a gel-like veterinary or pharmaceutical product.

2. Description of the Prior Art

There has recently been proposed a range of veterinary and pharmaceutical products which are dispensed in a gel-like form. The product is supplied in granular form and is mixed with water to form a water-based gel for administration to the patient. One of the primary applications is a veterinary product for oral administration to pigs and also other animals such as sheep, cattle, and horses. A requirement exists for a suitable cartridge for dispensing a product of this type.

SUMMARY OF THE INVENTION

According to the present invention there is provided a dispensing cartridge for a gel-like substance, comprising a body, a piston displaceable along the body to dispense gel-like substance from a forward end of the body, and a nozzle at the forward end of the body for dispensing the product upon displacement of the piston, the nozzle including means for preventing dripping of the gel upon inversion of the cartridge.

Preferably, dripping of the gel is prevented by forming the nozzle with an internal constriction and this may be achieved by forming the nozzle with a venturi-like internal profile. A venturi profile with a throat diameter of approximately 6 mm has been found to be effective.

Preferably the nozzle forms part of a removable cap applied to the forward end of the body.

Advantageously the piston has a forward face of a configuration which matches the configuration of the forward end of the interior of the body and cap in order to substantially obviate dead space within the body when the piston is in its forward-most position.

BRIEF DESCRIPTION OF THE DRAWINGS

An embodiment of the invention will now be described by way of example only with reference to the accompanying drawings in which.

DESCRIPTION OF THE PREFERRED EMBODIMENTS

Figure 1:
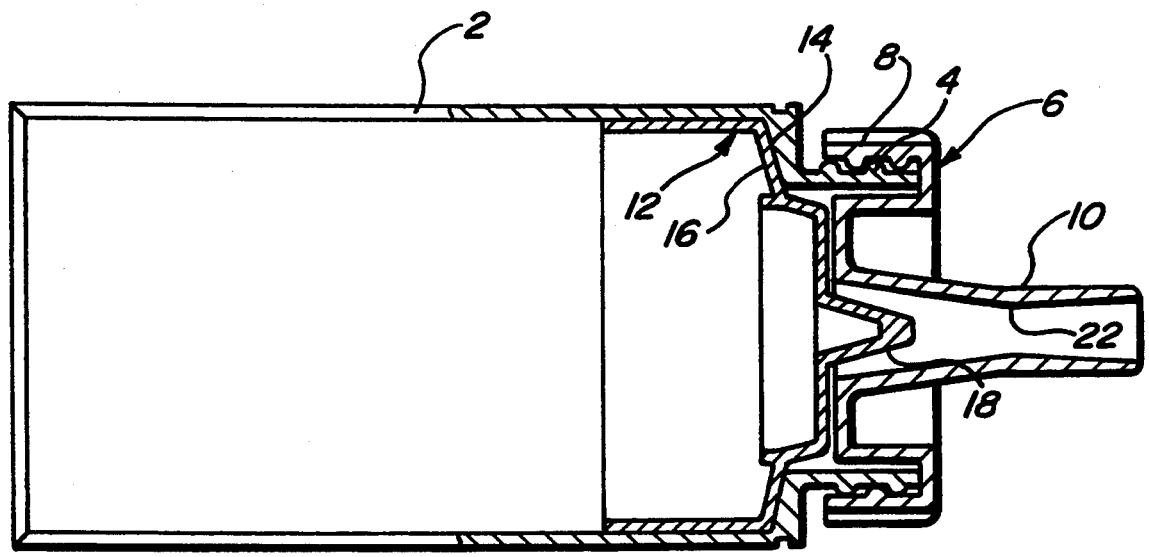
FIG. 1 is a longitudinal section of a cartridge in accordance with a preferred embodiment of the invention.
Figure 2:
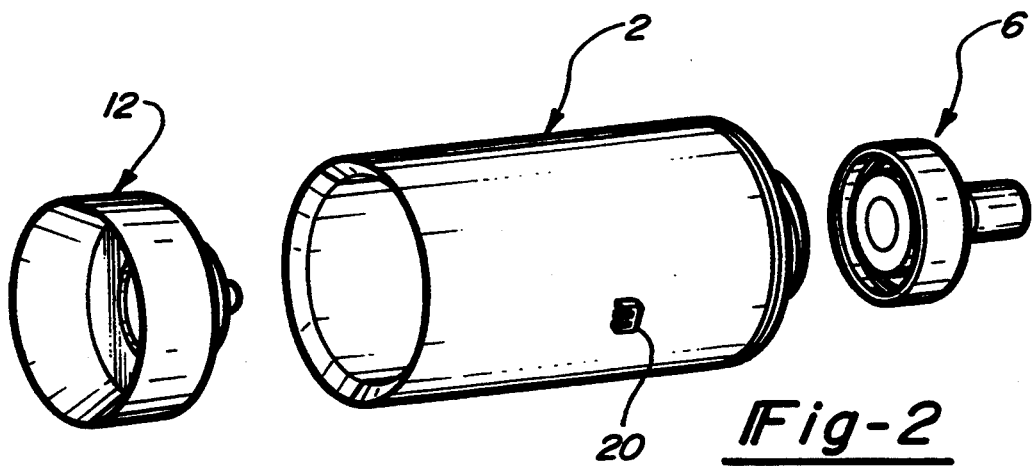
FIG. 2 is an exploded view of the cartridge.

As shown in FIGS. 1 and 2, the cartridge comprises a generally cylindrical body 2 open at its rear end and having an externally threaded neck 4 at its forward end. The neck 4 carries a removable cap 6 having an internally-threaded skirt 8 which fits over the neck 4, and a forwardly-projecting nozzle 10 which opens into the interior of the body 2. The precise form of the nozzle 10 will be described subsequently.

The body 2 contains a plunger or piston 12 movable from a position adjacent the rear end of the body 2 in order to dispense a gel-like product through the nozzle 10. The cartridge is adapted to be fitted into a dispensing gun of the type comprising a push rod which is advanced in discrete steps upon actuation of a trigger, the head of the push rod engaging the piston 12 of the cartridge in order to push the piston forwardly at each actuation of the trigger. For this purpose, the piston of the cartridge is of hollow construction open to the rear in order to receive the head of the push rod. The forward face of the piston is shaped with a configuration which closely matches the profile of the forward end of the interior of the cartridge so that when the piston 12 is in its forward-most position, with the face of the piston 12 in abutment with a shoulder 14 at the forward end of the cartridge, there is very little dead space remaining within the cartridge forwardly of the piston. This ensures that substantially all of the product within the cartridge can be dispensed. In particular, it will be seen that the inside face of the shoulder 14 at the forward end of the cartridge is inclined, with the peripheral portion 16 of the piston being similarly inclined and, radially inwardly of the shoulder 14, the piston 12 projects forwardly to a position very close to the inside face of the removable cap 6. The central portion of the piston 12 in alignment with the nozzle 10 includes a forwardly-projecting spigot 18 which projects into the nozzle.

Preferably, the cartridge fits into the body of the gun by a bayonet type fitting and for this purpose the body 2 includes one or more lugs 20 on its outer surface for reception into appropriate slots in the body of the gun by a bayonet type action of axial movement of the cartridge body followed by slight angular rotation.

As discussed earlier, the product to be dispensed from the cartridge is a gel-like product formed by mixing granules of a gel-forming substance with water. Mixing will usually be performed by the user and for this purpose, the cap 6 of the cartridge is removed, the piston 12 is pushed to the rear end of the cartridge, an appropriate measure of granular material and water is put into the cartridge, the cap is reapplied and the cartridge is shaken in order to mix the granules and water and thereby effect gel formation.

In order to prevent dripping of the gel through the nozzle 10 when the cartridge is inverted, the nozzle 10 is formed with an internal restriction 22 which prevents flow of the gel except when the gel is under pressure generated by advance of the piston 12. In the form shown, this restriction is provided by a venturi profile for the nozzle, the narrow throat of the venturi forming a constriction which will block flow of the gel except when under pressure. In one practical embodiment of the invention, the inlet to the nozzle 10 has a diameter of approximately 11 mm, the outlet has a diameter of approximately 7 mm and the narrow throat portion has a diameter of approximately 6 mm. A throat diameter of approximately 6 mm has been found to achieve effective blocking of the gel.

Figure 3:
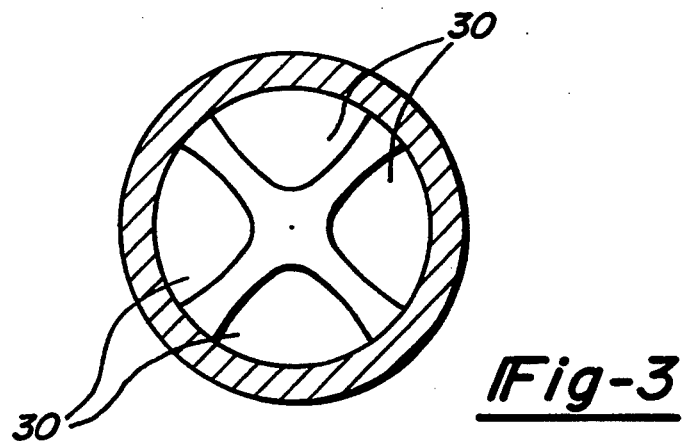
FIG. 3 is a section through a modified form of nozzle of the cartridge.

In a modification shown in FIG. 3, the throat portion of the nozzle 10 comprises two or more flexible petals 30, which form valve flaps extending radially into the passage of the nozzle. The valve flaps flex forwardly under the pressure of the product being discharged, to permit flow of the product through the nozzle. However, in a non-pressurised state the flaps will assume the configuration shown in which they restrict the size of the throat portion and block flow of the product even if the product has a lower viscosity than a gel. The valve flaps may be integrally moulded with the nozzle, from a suitable plastic material.

The embodiment has been described by way of example only and modifications are possible within the scope of the invention.

I claim:

1. A dispensing cartridge for a gel-like substance, comprising a body defining a bore, a piston received within and displaceable along said bore of said body to dispense gel-like substance from a forward end of the body, and a nozzle at the forward end of the body for dispensing the product upon displacement of the piston, the nozzle including a venturi section sized for preventing dripping of the gel upon inversion of the cartridge and when pressure is not applied to said piston.

2. A cartridge according to claim 1, wherein the venturi section has a throat diameter of approximately 6 mm.

3. A cartridge according to claim 1, wherein the piston has a forward end face which matches the configuration of the forward end of the interior of the body so as to substantially obviate any dead space within the body when the piston is in its forward-most position.

4. A cartridge according to claim 5, wherein the piston includes a forwardly-projecting spiggot which extends into the interior of the nozzle when the piston is in its forward-most position.

* * * * *